United States Patent [19]

Schulze et al.

[11] 4,110,371
[45] Aug. 29, 1978

[54] PREPARATION OF OXYDICARBOXYLIC ACID SALTS

[75] Inventors: Heinz Schulze; Edward T. Marquis, both of Austin, Tex.

[73] Assignee: Texaco Development Corporation, New York, N.Y.

[21] Appl. No.: 806,981

[22] Filed: Jun. 16, 1977

Related U.S. Application Data

[63] Continuation-in-part of Ser. No. 632,034, Nov. 4, 1975, abandoned.

[51] Int. Cl.$^2$ ............................................. C07C 59/12
[52] U.S. Cl. ........................... 260/531 C; 260/535 P
[58] Field of Search ..................... 260/535 P, 531 C; 560/239

[56] References Cited

U.S. PATENT DOCUMENTS

| | | | |
|---|---|---|---|
| 2,094,297 | 9/1937 | Joshua et al. | 560/239 |
| 2,145,097 | 1/1939 | Scott | 560/239 |
| 2,384,817 | 9/1945 | Chitwood | 260/531 C |
| 2,659,754 | 11/1953 | Ash et al. | 260/535 P |
| 2,886,590 | 5/1959 | Montgomery | 260/531 R |
| 3,431,298 | 3/1969 | Saotome et al. | 260/535 P |
| 3,790,625 | 2/1974 | Vogt et al. | 260/535 P |
| 3,870,749 | 3/1975 | Danesh | 260/535 P |

*Primary Examiner*—Paul J. Killos
*Attorney, Agent, or Firm*—Carl G. Ries; Thomas H. Whaley; Walter D. Hunter

[57] ABSTRACT

Oxyethylene dicarboxylic acid alkali metal salts are prepared from the corresponding oxydiethylene or polyoxyethylene diol and an aqueous alkali metal hydroxide in the presence of a catalytically effective amount of a nickel-copper-chromia catalyst at temperatures from about 200 to 300° C and pressures sufficient to maintain the reactants and products substantially in liquid phase. Preferably, the disodium salt of oxydiacetic acid is prepared by the oxidation of diethylene glycol with an aqueous sodium hydroxide solution in the presence of a catalytically effective amount of the nickel-copper-chromia catalyst. The disodium oxydiacetate can be readily precipitated from the crude reaction mixture by addition of a mixture of methanolisopropanol with subsequent filtration.

9 Claims, No Drawings

PREPARATION OF OXYDICARBOXYLIC ACID SALTS

This application is a Continuation-In-Part of application Ser. No. 632,034, filed Nov. 4, 1975, now abandoned.

BACKGROUND OF THE INVENTION

1. Field of the Invention

This invention relates to the production of alkali metal salts of oxy-substituted polycarboxylic acids, and more particularly to a method of preparation of alkali metal salts of oxyethylene dicarboxylic acids directly from the corresponding oxyethylene diols.

2. Prior Art

Caustic oxidation of aminoalkanols to the corresponding aminocarboxylic acid salts is known. See for example U.S. Pat. Nos. 3,535,373, 3,535,374, 3,535,375, and 3,842,081. Recently it has been disclosed in U.S. Pat. No. 3,717,676 that oxycarboxylic acid alkali metal salts can be prepared from the corresponding polyoxy-substituted primary alcohol and an alkali metal hydroxide in the presence of a cadmium catalyst.

It has now been discovered that alkali metal salts of oxyethylene dicarboxylic acids can be easily and effectively prepared by oxidizing the corresponding oxyethylene diol with an alkali metal hydroxide in the presence of a nickel-copper-chromia catalyst. Surprisingly, the process is very selective to oxyethylene diols. Monohydric oxy-substituted materials, such as butoxyethanol are not converted to the corresponding acid salt in accordance with the instant process.

SUMMARY OF THE INVENTION

In accordance with the broad aspect of the instant invention, alkali metal salts of dicarboxylic acids having the formula:

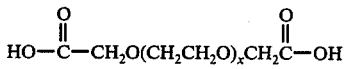

wherein $x$ is from 0 to about 4, are produced by heating the corresponding oxyethylene diol with an alkali metal hydroxide in the presence of an effective amount of a nickel-copper-chromia catalyst at temperatures in the range of from about 200° C. to about 300° C. and at pressures sufficient to maintain the reactants and products substantially in liquid phase.

DETAILED DESCRIPTION OF THE PREFERRED EMBODIMENTS

In accordance with a preferred embodiment, diethylene glycol (hydroxyethoxyethanol) and aqueous sodium hydroxide are admixed and reacted in the presence of a catalytically effective amount of nickel-copper-chromia catalyst under an inert nitrogen atmosphere at temperatures in the range from about 225° C. to about 275° C. and pressure of about 1,000 psi to about 4,000 psi to produce disodium oxydiacetate. The disodium oxydiacetate is recovered by admixing a methanol-isopropanol mixture with the crude reaction mixture to precipitate the salt. The precipitate is then separated by standard filtration techniques.

The oxyethylene diols useful in the practice of the instant invention can be depicted by the formula:

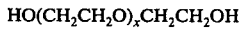

wherein $x$ is an integer from 1 to about 5. Preferred diols are diethylene glycol, triethylene glycol and tetraethylene glycol. The most preferred glycol is diethylene glycol. The hydroxides that can be used in accordance with the instant invention may be any of the well known alkali metal hydroxides or mixtures thereof. From a cost standpoint, sodium hydroxide is preferred. The catalyst utilized in this process is a nickel-copper-chromia catalyst as described in U.S. Pat. No. 3,152,998, issued Oct. 13, 1964.

In accordance with this invention, the catalyst employed comprises in combination the metals and oxides of nickel and copper and chromium oxide. More particularly, the catalyst is characterized by having the composition calculated in mole percent on an oxide-free basis of 60 to 85% nickel, 14 to 37% copper and 1 to 5% chromium with the preferred proportions being 72 to 78% nickel, 20 to 25% copper and 1 to 3% chromium.

An important feature of the catalysts of this invention is the extent to which the reducible oxide components have been reduced to metal, it being understood that the chromium oxide is not affected under the reducing conditions employed. Surprisingly, it has been found that high yields of the desired products may be obtained provided that the catalyst composition has been treated so that the amount or percent of reduced nickel is at least 30%.

The catalysts of this invention are produced by preparing a finely divided mixture of the metal oxides according to well known methods wherein the components on a metal basis correspond to the proportions specified above. This mixture of metal oxides is mechanically converted, e.g. compressed or extruded, to the desired physical shape. Pellets are the preferred physical shape with sizes such as ⅛ inch by ⅛ inch and ⅛ inch by 3/16 inch being more suitable. This performed catalyst mixture may be prepared with a small amount of a die lubricant to facilitate preparation of the pellets.

As noted above, the preformed or pelleted catalysts immediately after formation are not mechanically or physically stable. Water, for example, can cause the nickel-copper-chromia catalyst to disintegrate very quickly. These catalysts must be reduced by treatment with hydrogen at an elevated temperature until the percent of metallic nickel based on the total catalyst weight is at least 30% and preferably at least 35%. Ordinarily, reduction is effected at a temperature in the range of 250 to 400° C. while hydrogen is continuously passed over or through the catalyst, with temperatures from 300 to 320° C. being preferred for the reduction. Depending on the quantity of catalyst being treated, reduction may be completed in a short time or may require an extended period of many hours. A much large proportion than 30% of the nickel may be reduced with desirable results. Thus, effective physically-stable catalyst may be prepared having as much as 85% reduced nickel.

The metal oxides, or mixtures thereof, used in producing the instant catalysts may be prepared by well known methods. For example, soluble salts, such as the nitrates of nickel, copper and chromium, may be prepared in an aqueous solution and precipitated therefrom as carbonates by the addition of solid ammonium carbonate. An excess of about 5% of the ammonium carbonate is preferred in this step. The precipitated catalyst composition is filtered, washed with water and dried at about 110° C. This material is then calcined in the presence of air desirably at a temperature in the range of 350 to 400° C. until the carbonate salts have been converted to the corresponding oxides.

If desired, the nickel-copper-chromia catalyst pellets after being subjected to the reduction step previously described can be finely ground to about 80 to 200 mesh size for use in the process of this invention.

In general the salts produced by the instant inventive process are known oxy containing diacetates. These salts are useful as chelating agents. Additionally, upon acidification, the corresponding free acids are produced. In general, these acids undergo all the reactions characteristic of carboxylic acids. Various uses of these compounds are disclosed in "Diglycolic Acid," *I & E Chemistry*, August 1949, p. 1653 et seq.

The process of the instant invention can be carried out in batch or on a continuous scale. Generally effective temperatures are from about 200 to 300° C. with 225 to 275° C. being preferred. Effective pressures can generally be described as autogenous. Pressures in the range of from about 1,000 to 4,000 psi are usually sufficient to maintain the reaction medium substantially in liquid phase.

The diols and the alkali metal hydroxide can be present in the reaction medium in approximately equal stoichiometric amounts; however, a molar excess of sodium hydroxide is preferred. At least a 10 mole percent excess of the alkali metal hydroxide should be utilized. Thus, for a diol (functionality 2.0), 2.2 moles of the alkali metal hydroxide is required.

The amount of the nickel-copper-chromia catalyst employed is that amount effective in catalyzing the reaction of the instant process. General considerations include the catalyst surface area, the reactants, the concentration of reactants, and the mode of carrying out the process, i.e., batch or continuous. The exact amount of catalyst for any given set of conditions can be readily determined by the skilled artisan without undue experimentation in that the amount is not critical.

Although the reaction can be carried out under anhydrous conditions, it is preferable to utilize water as a solvent to prevent precipitation of the formed salt. The amount of water utilized is not critical. Generally, sufficient water is utilized to maintain a substantially homogeneous reaction mixture. The water can be conveniently introduced into the reaction medium by using an aqueous alkali metal hydroxide solution. Aqueous solutions of from about 50% by weight to about 75% by weight metal hydroxide have been found adequate.

It will be realized by the skilled artisan that use of the higher oxyethylene materials such as triethylene glycol, tetraethylene glycol and polyoxyethylene glycol results in some cleavage of the ether bonds to yield a mixture of lower oxyethylene dicarboyxyclic acid salts.

One of the advantageous aspects of the instant invention, in light of the prior art, is that the amount of water present in the reaction medium does not appear deleterious to the reaction. Therefore, as opposed to prior known methods, the amount of water in the reaction medium need not be rigorously controlled or calculated.

Once the reaction has proceeded to completion the acid salt product can be recovered from the crude reaction mixture by known methods. Recrystallization of the formed diacid salt or extraction of the acidified diacid with a suitable solvent are exemplary of such known methods. Preferably, the diacid salt product is recovered by precipitation and subsequent filtration. In accordance with this methods, an excess of a methanolisopropanol mixture is admixed with the crude reaction product to precipitate the diacid salt. The admixture is then filtered by standard means to isolate thhe precipitate which is the product.

The following examples are given by way of illustration and not meant as limitations.

EXAMPLE I

In a clean, dry, stirred, Hastelloy B autoclave fitted with a back pressure regulator (1,300 psig) and a Monel liner was charged 214.0 grams of diethylene glycol (2.0 moles), 240.0 grams sodium hydroxide (6.0 moles), 250 ml water and 30 grams of a freshly ground nickelcopper-chromia catalyst prepared as previously described and having a particle size ranging from about 80 to about 200 mesh. After sealing, the clave was flushed with nitrogen, and the contents heated to a temperature of 250 to 251° C. where it was maintained for about 17 minutes. Upon cooling, the reactor effluent was diluted with sufficient water to facilitate filtration and filtered through a sintered glass funnel to remove the catalyst. The clear filtrate was then concentrated by stripping. Excess methanol was then added to the concentrate to form a precipitate which on recovery was analyzed by NMR(Nuclear Magnetic Resonance). The analysis showed the following:

Selectivity (moles SODA [1]/moles DEG [2] reacted) 90.0%
Conversion (moles DEG reacted/moles DEG charged) 89%
Yield (moles SODA/moles DEG charged) 80%

1) Disodium oxydiacetate
2) Diethylene glycol

The isolated product showed an actual yield of 71.5% disodium oxydiacetate. Less than 0.5 parts per million nickel was detected by Atomic Absorption in the filtrate.

EXAMPLE II

Following the procedure of Example I, 214.0 grams diethylene glycol (2.0 moles), 240.0 grams sodium hydroxide (2.0 moles), 240 ml water and 35.0 grams of the same nickel-copper-chromia catalyst as employed in Example I were treated for 10 minutes at 237 to 265° C. NMR spectral data of the aqueous filtrate indicated a 96° conversion of diethylene glycol and a 91° selectivity to the disodium oxydiacetate product. Atomic absorption analysis of the aqueous filtrate indicated the essential absence of dissolved or chelated metal as follows: Ni, <0.7ppm; Cu, <0.5 ppm; chromium, <0.4 ppm.

EXAMPLE III

Following the procedure of Example I, 226 grams triethylene glycol (1.5 moles), 180 grams sodium hydroxide (4.5 moles), 180 ml of water and 30 grams of the same freshly ground nickel-copper-chromia catalyst as used in Example I were heated for 12 minutes at 250 to 253° C. After catalyst removal from the aqueous filtrate, NMR spectral analysis showed the following:

Selectivity to

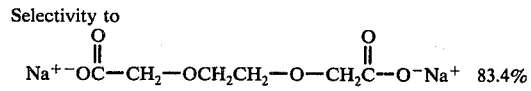 83.4%

Yield of the above product was 76.6% and the conversion of triethylene glycol 92%.

EXAMPLE IV

In this example, a tetraethylene glycol was converted to the corresponding disodium salt in accordance with the process of the invention. Again, following the producedure of Example I, 294 grams tetraethylene glycol (1.5 moles), 180 grams sodium hydroxide (4.5 moles), 180 ml of water and 30 grams of the same freshly ground nickel-copper-chromia catalyst as used in Example I were heated at 284° to 297° C. for 20 minutes. After catalyst removal from the aqueous filtrate, NMR spectral analysis showed the following:

Selectivity to
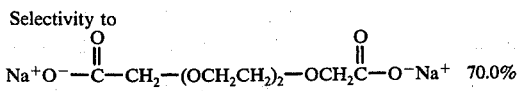 70.0%

Yield of the above product was 63.3% and conversion of tetraethylene glycol 90.5%.

EXAMPLE V

In this comparative example Raney nickel catalyst (prepared according to organic synthesis Coll., Vol. 2, p. 181) was used. Following the procedures of Example I (except that no back pressure regulator was used), the reactants were heated 40 minutes at 192 to 251° C. A final pressure of 2,700 psi was attained. Upon cooling, the reaction mixture was diluted with 200 ml of water filtered and the filtrate stripped until the weight of residue was 235 grams. The resulting slurry was precipitated with a methanol-isopropanol mixture consisting of 400 ml methanol and 250 ml isopropanol by stirring 4 hours at ambient temperature. The resulting heterogeneous mixture was filtered and washed five times with a 1:1 (by volume) mixture of methanol and isopropanol and dried at 140° C. in high vacuum. The residue recovered weighed 108.5 grams. NMR analysis indicated that substantially the total yield was sodium oxydiacetic acid (% yield = 30.4). The chelating power of the recovered product was shown to be about 196 milligrams $CaCO_3$ per gram product.

The results obtained in this example illustrate the low yield of the desired oxydiacetic acid achieved when using the art-recognized Raney nickel catalyst.

EXAMPLE VI

This example shows the catalytic effect of nickel in accordance with the instant invention. Using the procedure of Example I, 214.0 grams diethylene glycol (2.0 moles), 280.0 grams sodium hydroxide (7.0 moles) and 200 ml water were heated for 23 minutes at 229 to 309° C. at a pressure of 1,375 psig maintained by a back pressure valve regulator. The product was worked up substantially by the procedure of Example I. NMR spectral data of the aqueous filtrate indicated a 97.6% conversion of diethylene glycol but a selectivity of only 18.5% to the desired disodium oxydiacetate. The bulk of the reaction product was sodium acetate and sodium oxalate.

EXAMPLE VII

This example shows the unexpected selectivity of the instant process to oxyethylene diols. Substantially in accordance with the procedure of Example I, 238 grams of ethylene glycol monobutyl ether (2.0 moles), 160 grams sodium hydroxide (4.0 moles), 200 ml of water and 300 grams of the same freshly ground nickel-copper-chromia catalyst as utilized in Example I were heated to 312° C. Very little hydrogen evolution was detected. The reaction product mixture was worked up substantially as in Example I and the NMR analysis of the aqueous filtrate showed the presence of only unreacted ethylene glycol monobutyl ether (starting material) and unverified traces of acetic acid.

EXAMPLE VIII

In this example disodium oxydiacetate was prepared in a continuous process. A tubular reactor consisting of a 1″ I.D., 41 inch long Monel pipe was fitted with a thermowell inserted in the center of the tubular reactor with four thermocouples located at varying lengths along the reactor and a back pressure regulator set at 1,500 psig. The reactor was packed with pelleted nickel-copper-chromia catalyst. Separate feeds of diethylene glycol and a 40% aqueous sodium hydroxide solution were pumped to the bottom of the reactor which was fitted with a Monel cross through which the feed entered the reactor. Diethylene glycol was pumped to the reactor at the rate of about 0.6 pounds per hour and the 40% NaOH solution at the rate of 2.42 pounds per hour such that the respective mole ratio of DEG:NaOH was 2.74:10.98. The reaction temperature reached an average of about 260° C. with this measurement varying slightly over the thermocouple locations. Space velocity of grams feed/milliliter catalyst per hour was 2.56. The effluent was diluted with water and filtered. NMR analysis showed the following:

| | |
|---|---|
| Conversion of DEG | 74.4% |
| Selectivity of SODA | 86.2% |
| Yield of SODA | 64.1% |

While the invention has been explained in relation to its preferred embodiment, it is to be understood that various modifications thereof will become apparent to those skilled in the art upon reading the specification and is intended to cover such modifications as fall within the scope of the appended claims.

What is claimed is:

1. A process for producing metal salts of dicarboxylic acids having the formula:

wherein $x$ is from 0 to about 4, directly from the corresponding oxyethylene diol comprising the step of:
heating said oxyethylene diol with an alkali metal hydroxide in the presence of a catalytically effective amount of a nickel-copper-chromia catalyst at temperatures in the range of from about 200° C. to about 300° C. and at pressures sufficient to maintain the reactants and products substantially in liquid phase.

2. The process of claim 1 wherein said oxyethylene diol is selected from the group consisting of diethylene glycol, triethylene glycol and tetraethylene glycol.

3. The process of claim 1 wherein the said alkali metal hydroxide is selected from the group consisting of sodium hydroxide, potassium hydroxide and mixtures thereof.

4. The process of claim 1 wherein the said nickel-copper-chromia catalyst is prepared from a mixture of oxides of nickel, copper and chromium wherein the proportions of the metals in said mixture, calculated on an oxide free basis, are 60 to 85 mole percent nickel, 14 to 35 mole percent copper and 1 to 5 mole percent chromium and wherein the nickel and copper oxides in the said mixture are reduced by contacting the mixture with hydrogen at a temperature within the range from about 250 to 400° C. until the percentage of reduced nickel is from 30 to 100 percent.

5. The process of claim 1 wherein the said nickel-copper-chromia catalyst is in pellet form made by first forming pellets prepared from a mixture of oxides of nickel, copper and chromium wherein the proportions of the metals in said mixture, calculated on an oxide free basis, are 60 to 85 mol. percent nickel, 14 to 37 mole percent copper and 1 to 5 mole percent chromium and wherein the nickel and copper oxides in the said pellets are reduced by contacting the mixture with hydrogen at a temperature within the range from about 250° to about 400° C. until the percentage of reduced nickel is from 30 to 100 percent.

6. The process of claim 1 wherein the said nickel-copper-chromia catalyst is the catalyst of claim 5 reduced in size to a finely-divided form having a mesh size of about 80 to about 200.

7. A process for producing an alkali metal oxydiacetate comprising the step of:
heating diethylene glycol with an aqueous alkali metal hydroxide solution in the presence of a nickel-copper-chromia catalyst at temperatures in the range of from about 200° C. to 300° C. and pressures sufficient to maintain the products and reactants substantially in liquid phase.

8. The process of claim 7 wherein said aqueous alkali metal hydroxide solution is a 50 to 70 weight percent sodium hydroxide solution, wherein said temperature is from about 225° C. to 275° C.; and, wherein said pressure is in the range of from 1,000 psi to about 4,000 psi.

9. The process of claim 7 comprising the further steps of:
precipitating said alkali metal oxydiacetate by adding to the reaction mixture of the first step an excess of a methanol-isopropanol mixture; and
filtering the resultant mixture to isolate said precipitate.

* * * * *